United States Patent
Horikawa et al.

(10) Patent No.: US 6,508,803 B1
(45) Date of Patent: Jan. 21, 2003

(54) NITI-TYPE MEDICAL GUIDE WIRE AND METHOD OF PRODUCING THE SAME

(75) Inventors: Hiroshi Horikawa, Kanagawa (JP); Kaisuke Shiroyama, Kanagawa (JP); Kengo Mitose, Kanagawa (JP)

(73) Assignees: Furukawa Techno Material Co., Ltd., Hiratsuka (JP); The Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 09/581,521

(22) PCT Filed: Nov. 5, 1999

(86) PCT No.: PCT/JP99/06184

§ 371 (c)(1), (2), (4) Date: Jul. 6, 2000

(87) PCT Pub. No.: WO00/27462

PCT Pub. Date: May 18, 2000

(30) Foreign Application Priority Data

Nov. 6, 1998 (JP) ............................................. 10-316690
Sep. 27, 1999 (JP) ........................................... 11-273470

(51) Int. Cl.⁷ ............................................. A61M 25/00
(52) U.S. Cl. .................. 604/523; 604/164.13; 600/434; 600/585
(58) Field of Search ........................... 604/95.03–95.05, 604/164.13, 523–525; 600/434, 585

(56) References Cited

U.S. PATENT DOCUMENTS 5,069,226 A * 12/1991 Yamauchi et al. ....... 604/95.05
5,230,348 A    7/1993 Ishibe et al.

FOREIGN PATENT DOCUMENTS

| JP | 02024550 | 5/1950 |
| JP | 02024548 | 1/1990 |
| JP | 02024549 | 1/1990 |
| JP | 06083726 | 10/1994 |
| WO | WO97/18478 | 5/1997 |

* cited by examiner

Primary Examiner—Anhtuan T. Nguyen
Assistant Examiner—Michael M Thompson
(74) Attorney, Agent, or Firm—Oblon, Spivak, McClelland, Maier & Neustadt, P.C.

(57) ABSTRACT

A medical guidewire comprised of an NiTi-based alloy having a high elasticity over a wide range of strain, excellent straightness, and preferable shape and characteristics of a stress-strain curve in a tensile test. The wire is obtained by applying a predetermined tension to a cold drawn NiTi-based alloy wire and mechanical straightening it under conditions of a predetermined torsional shear strain and temperature and shows superior pushability, torque transmission, and reinsertability as a medical guidewire, so is preferable for a catheter guidewire, endoscope guidewire, etc.

9 Claims, 10 Drawing Sheets

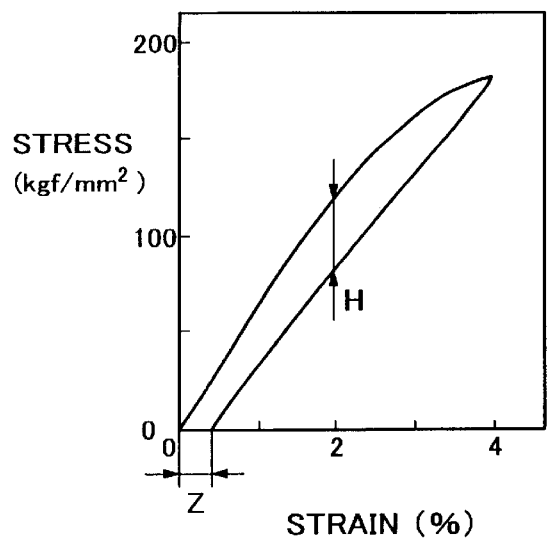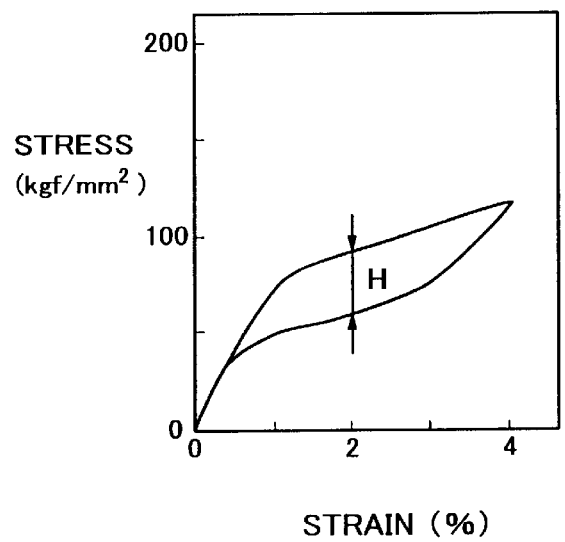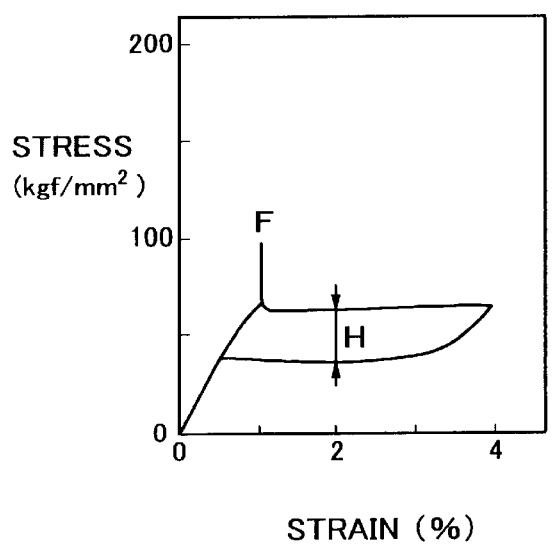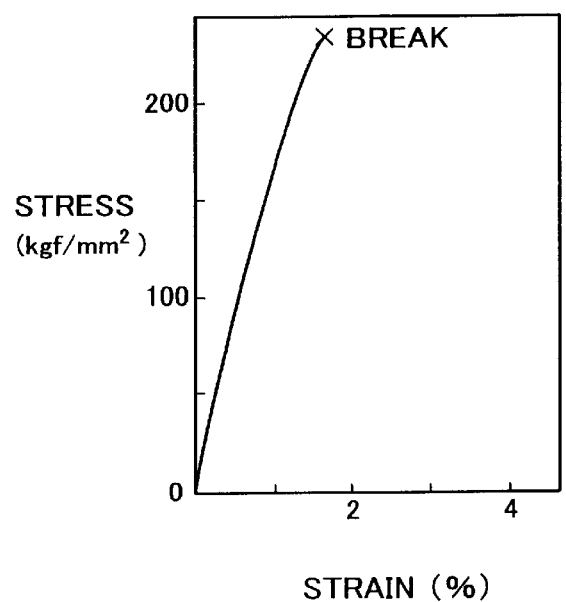

NITI-TYPE MEDICAL GUIDE WIRE AND METHOD OF PRODUCING THE SAME

TECHNICAL FIELD

The present invention relates to a medical guidewire comprised of an NiTi-based alloy having a high elasticity over a wide range of strain and a method of producing the same, more particularly relates to a catheter guidewire etc. made of an NiTi-based alloy wire having a straightness, and shape and characteristics of a stress-strain curve preferable for a medical guidewire.

BACKGROUND ART

Medical guidewires include catheter guidewires and endoscope guidewires. Here, the explanation will be given taking as an example a catheter guidewire.

A catheter guidewire is used for guiding a catheter (thin tube) for treatment or examination into a blood vessel and leaving it in the affected area.

Therefore, a catheter guidewire is required to have enough flexibility and shape recovery for insertion into branched and meandering blood vessels without damaging them by conforming to the shape of the blood vessels. The demand for this characteristic has become much stronger in recent years as catheters are now being introduced close to the end of blood vessels.

In the past, stainless steel wire has been used for the catheter guidewire, however it suffers from the disadvantage that stainless steel wire permanently deforms when passed through a sharply curved blood vessel. The wire ends up remaining curved and can no longer proceed further or cannot be reinserted.

Therefore, three types of wire have been recently proposed: (1) a superelastic wire using the superelasticity of an NiTi-based alloy (Japanese Examined Patent Publication (Kokoku) No. 2-24550, Japanese Examined Patent Publication (Kokoku) No. 2-24548, and Japanese Examined Patent Publication (Kokoku) No. 2-24549), (2) a wire obtained by cold drawing an NiTi-based alloy and then heat treating it at a low temperature (hereinafter referred to as "cold drawn, low temperature heat-treated wire") (Japanese Examined Patent Publication (Kokoku) No. 6-83726 and U.S. Pat. No. 5,230,348), and (3) a cold drawn wire obtained by only cold drawing (WO97/18478).

The above superelastic wire of type (1) utilizes the characteristic that deformation caused by stress-induced martensitic transformation is recovered by reverse transformation when unloaded, so it is much more flexible compared with conventional stainless steel wire and has a strong shape recovery, i.e., so-called superelasticity.

Note that superelasticity is given by heat treatment (shape memory heat treatment, for example, 400 to 500° C.) for giving superelasticity after cold drawing.

Superelastic wire, however, has a yield point F on the stress-strain curve as shown in FIG. 1D. Stress is not increased even if more strain is given when exceeding the point, so there are the disadvantages that the wire is poor in pushability, cannot be inserted close to an end of the blood vessel, does not allow rotation by the holder to be easily conveyed to the tip of the wire, and therefore is poor in operability (torque transmission).

Also, cold drawn, low temperature heat-treated wire of type (2) is produced by shaping an NiTi-based alloy wire having a cold working rate of 35 to 50% to make it straight (for example, holding it at 350 to 450° C. for 10 to 30 minutes). As shown in the stress-strain curve of FIG. 1C, almost no stress-induced martensitic transformation or reverse transformation occurs and the apparent modulus of elasticity is large, so the pushability is excellent.

However, there is a large stress difference H, between loading and unloading, at a strain of 2% after applying strain up to 4%, then unloading. Simultaneously, sufficient straightness cannot be obtained by shaping. Therefore, the torque transmission declines.

The cold drawn wire of type (3) has the advantage, as shown in FIG. 1B, that the apparent modulus of elasticity is larger than that of the (2) cold drawn, low temperature heat-treated wire, however, since there is a large residual strain after deformation, the wire ends up permanently deforming when passed through a curved blood vessel.

Further, just cold working is not enough to obtain a wire having a high straightness, so the torque transmission is poor. Also, in spite of the high modulus of elasticity, since the straightness is low, the pushability is inferior for the high modulus of elasticity. Further, there is a large residual strain and therefore a problem in reusability. Especially, in wires of the types (2) and (3), the low straightness is a problem. Improvement of this point has been desired.

As explained above, the conventional superelastic type wire, low temperature heat treated type wire after cold drawing cold drawn type wire do not show the sufficient characteristics for use as a medical guidewire. Development of a wire superior in all of the pushability, torque transmission, and reusability required for use as a medical guidewire has therefore been desired.

SUMMARY OF THE INVENTION

In view of this background art, the present inventors closely analyzed the relationship between characteristics in use required for a medical guidewire and mechanical characteristics of the guidewire and discovered that the required characteristics of the above guidewire can be secured by giving the guidewire specific mechanical characteristics and therefore attempted to give a guidewire a specific shape and characteristics of a stress-strain curve as determined by tensile tests.

Namely, the present inventors read a variety of characteristics from the stress-strain curve as determined by the above tensile tests and found the relationship between the characteristics of the wire and the characteristics in use required for medical guidewire.

Then, they found that the straightness of the wire and the following four characteristics, that is, a total of five characteristics, are closely related with a medical guidewire.

Among the five characteristics, the (1) straightness has to be good from both the viewpoints of reusability (insertability) and torque transmission when used as a medical guidewire.

The other four characteristics are the shape and characteristics of the stress-strain curve as found by tensile tests of the wire, that is, (2) the shape, (3) the apparent modulus of elasticity, (4) the stress difference (that is one of the parameters with reference to stress hysteresis) at a constant strain (strain of 2%) between loading and unloading of a load, and (5) strain recovery after removing strain (residual strain).

Here, the maximum strain at the tensile tests was made 4%. The stress-strain curve was obtained by giving 4% strain, then reducing the load to 0.

The reason why the maximum strain was made 4% in this way was that by conducting a tensile strength test up to a strain of 4%, it is possible to obtain sufficient information enabling evaluation of the material characteristics under the standard conditions of use of medical guidewire.

The inventors conducted further studies and as a result learned that the relationship between the characteristics (1)

to (5) of wire and characteristics in use of medical guidewire becomes as follows:

Namely, the pushability is affected by the above (2) and (3). The (2) shape of the stress-strain curve should be one of a monotonous increase in stress v.s. strain without any yield points or inflection points. A guidewire like the conventional superelastic wire which has a yield point and where the gradient of the stress with respect to the strain decreases when the yield point is exceeded easily buckles in a blood vessel and is difficult to push further in. A guidewire which has a high (3) apparent modulus of elasticity has stiffness as a wire and can be easily inserted further.

Further, the torque transmission is affected by the characteristics (1) and (4). A guidewire which has a low (1) straightness has a larger frictional force with the inner wall of the blood vessel. The torque is no longer transmitted accurately and the guidewire cannot be inserted close to the end of the blood vessel with good operability. Also, a guidewire which has a large (4) stress difference is slow to turn at its tip portion in response to rotation of the wire by the physician at its holder.

Also, when looking at repeated insertability (reusability), the smaller the (5) residual strain, the more the insertion can be repeated to the same patient. It is necessary to significantly reduce the residual strain for enabling repeated insertion.

The present inventors engaged in in-depth studies based on the above discoveries and thereby completed the present invention.

Accordingly, an object of the present invention is to solve the above problems and to provide an NiTi-based alloy wire having high elasticity characteristics over a wide range of strain and the above characteristics (1) to (5) and thereby provide an NiTi-based medical guidewire displaying excellent pushability, torque transmission, and repeated insertability when used as a medical guidewire.

Another object of the present invention is to provide a method of producing a medical guidewire displaying the above characteristics.

The present invention will be explained in detail below.

A first aspect of the present invention relates to a medical guidewire.

Namely, the present invention provides a medical guidewire comprised of an NiTi-based alloy wire made of a wire produced by mechanically straightening a cold drawn NiTi-based alloy wire and (1) having a straightness of 20 mm/1.5 m as determined by the suspension method, and having a shape and characteristics of the stress-strain curve by a tensile test which satisfy the following requirements (2) to (5), and thereby displaying excellent pushability, torque transmission, and reusability as a medical guidewire.

Requirement (2) to (5):

(2) A monotonous increase in stress up to strain of 4% without any yield points or inflection points and no stress-induced martensitic transformation shown at all.

(3) High elasticity characteristics over a wide range of strain and an apparent modulus of elasticity of 3000 kgf/mm$^2$ or more at a strain of 4%.

(4) A residual strain after loading up to strain of 4% then unloading, is not more than 0.15%.

(5) A stress difference, between loading and unloading, at a strain of 2% during unloading after loading up to 4%, is not more than 15 kgf/mm$^2$.

The present invention will be explained in further detail below.

First, FIG. 2 is a view of a general stress-strain curve in a tensile test of an NiTi-based alloy. The yield point F, apparent modulus of elasticity $Ed=\sigma1/\delta1$, stress difference H, and residual strain Z used in the explanation of the present invention are defined as shown in the figure.

The guidewire of the present invention is produced by mechanical straightening a cold drawn NiTi-based alloy wire and then using the special process of production explained in detail later to obtain a wire having an excellent (1) straightness.

The straightness of the NiTi-based alloy wire of the present invention as determined by the suspension method is not more than 20 mm/1.5 m.

Here, the straightness is a value measured by the suspension method, that is, as shown in FIG. 3, a value. indicated by a distance b (mm) in the horizontal direction on a floor surface 3 between a tip position of a wire 2 tested when feeding out the wire 1.5 m from a wire fixing tube 4 and a tip position of a completely straight wire 1. Accordingly, the distance from the lower surface of the fixing tube 4 to the floor surface during the test varies in accordance with the bent condition of the wire.

The straightness of the wire has a large effect on the torque transmission of the characteristic of use of a medical guidewire. Namely, a wire having a high (excellent) straightness excels in torque transmission.

The inventors conducted experiments on the relationship between the wire straightness and the torque transmission using an apparatus shown in FIG. 4.

Namely, they found the torque transmission by twisting one end of a wire 2 passed through a loop-shaped polyethylene tube 5 by a drive (motor 6) for a predetermined angle (drive angle) and measuring the follow angle of the other end of the wire at that time by rotary encoders 7 and 8.

The tested samples are the samples shown in Table 3 of a first embodiment explained later, that is, Sample No. 1 (A. Wire of present invention, straightness of 19 mm), Sample No. 23 (B. Cold drawn wire, straightness of 105 mm), Sample No. 24 (C. Cold drawn, low temperature heat-treated wire, straightness of 70 mm), Sample No. 25 (D. Superelastic wire, straightness of 30 mm), and Sample No. 26 (E. Highly worked stainless steel wire, straightness of 30 mm).

The results of measurement of the torque transmission are shown in FIG. 5.

The wire A of the present invention having a high straightness has a drive angle and follow angle in a substantially 1:1 correspondence, and exhibits an excellent torque transmission. As opposed to this, the wires of the related art having a low straightness exhibited in delay in following drive. In particular, the cold drawn wire exhibited a large delay. This was due to the low straightness.

Next, the guidewire of the present invention had a shape and characteristics of the stress-strain curve in a wire tensile test, as shown in FIG. 1A, where the stress increases monotonously up to a strain of 4% with no yield points F or inflection points and no stress-induced martensitic transformation is exhibited at all.

Here, the fact that an NiTi-based alloy wire according to the present invention does not show any stress-induced martensitic transformation at all will be explained.

Differential scan calorimetry (DSC) was carried out for investigating the phase changes of an alloy wire for Sample No. 1 (A. Wire of present invention) shown in Table 3 of the first embodiment which will be explained later on and for Sample No. 24 (C. Cold drawn, low temperature heat-treated wire of the related art) and Sample No. 25 (D. Superelastic wire of the related art) for comparison. The results are shown in FIGS. 6A, 6C, and 6D.

The NiTi alloy wire of the present invention shown in FIG. 6A does not exhibit a peak indicating that a martensite phase transforms to a parent phase. Superelasticity and martensitic transformation have a close relationship with each other. A wire which does not undergo martensitic transformation does not exhibit superelasticity.

As opposed to this, the cold drawn, low temperature heat-treated NiTi alloy wire of the related art shown in (C) exhibited a slight but broad peak.

Also, the superelastic NiTi alloy wire of the related art shown in (D) clearly exhibited a peak indicating that the martensite phase transformed to the parent phase.

Furthermore, the inventors investigated the above three samples for phase transformation by X-ray analysis at −40° C., room temperature, and 60°. As a result, the NiTi alloy wire of the present invention failed to exhibit any changes corresponding to transformation between a parent phase and martensite phase in accordance with temperature at an X-ray peak.

On the other hand, the cold drawn, low temperature heat-treated and superelastic NiTi alloy wires of the related art were observed that of the X-ray peak is changed and the phase transformation appears due to a change of the temperature.

In this way, it was confirmed that the NiTi-based alloy wire according to the present invention did not exhibit any stress-induced martensitic transformation at all.

Next, the guidewire of the present invention exhibits the characteristics, as follows: (3) high elastic characteristics over a wide range of strain and a large apparent modulus of elasticity Ed [σ/δ(0.04)] of 3000 kgf/mm² or more at a strain of 4%, (4) a small stress difference H of less than 15 kgf/mm², between loading and unloading at a strain of 2% during unloading after loading up to 4%, and (5) a small residual strain Z of less than 0.15%.

Such an NiTi-based guidewire of the present invention is superior in the pushability, torque transmission, and re-insertability (reusability) required in use for a medical guidewire. The required characteristics are governed by (1) the straightness of the wire and the characteristics (2) to (5) in a stress-strain curve of wire tensile tests.

Table 1 shows the results of studies of the inventors regarding the relationship between the characteristics of a guidewire of the present invention and the pushability, torque transmission, and re-insertability (reusability) required when used as a medical guidewire.

inserted close to the end of the blood vessel. The smaller the strain Z, the more elastic the guidewire becomes and the more it can be reinserted.

Also, the smaller the stress difference H, the better the torque transmission and the better the controllability by the doctor. Furthermore, a high straightness of a wire improves the torque transmission.

Next, in the present invention, by making the apparent modulus of elasticity 350 kgf/m² or more at a strain of 4% and the residual strain-when loading up to a strain of 4% and then removing it less than 0.10%, the characteristics of a guidewire for medical use can be further exhibited.

The NiTi-based alloy wire of the present invention is chosen from the group of any of (1) an NiTi alloy containing 50.2 to 51.5 at % of Ni and a remainder of Ti, (2) an NiTi-based alloy containing 49.8 to 51.5 at % of Ni, 0.1 to 2.0 at % of one or more of Cr, Fe, V, Al, Cu, Co, and Mo, and a remainder of Ti, and (3) an NiTi-based alloy containing 49.0 to 51.0 at % of Ti, 5.0 to 12.0 at % of Cu, 0.1 to 2.0 at % of one or two kinds of Cr, Fe, V, Al, Co and Mo, and a remainder of Ni.

One application of a medical guidewire of the present invention is a catheter guidewire. The present invention can be used for all or part of a catheter guidewire.

Note that a guidewire of the present invention can be freely deformed by hand in hot water at 60° C. for shaping easy to be inserted into a blood vessel just by immersing the tip in.

[2] The second aspect of the present invention relates to a method of producing a medical guidewire according to the first aspect of the invention.

Namely, the present invention provides a method of producing a medical guidewire comprising by mechanical straightening a cold drawn NiTi-based alloy wire, while applying a tension of 18 kgf/mm² or more, under conditions of a torsional shear strain of 2 to 50%, a temperature of 100 to 275° C., and a range of abcdefg shown in FIG. 7 so as to obtain an NiTi-based alloy guidewire having the characteristics described in the above first aspect of the invention.

Below, a method of producing an NiTi-based medical guidewire of the present invention will be explained in detail.

The present invention is produced by successively hot working an NiTi-based alloy ingot, cold drawing a wire, and then mechanical straightening the wire.

TABLE 1

| Characteristics of guidewire | | | | | |
|---|---|---|---|---|---|
| (1) Straightness b | (2) Yield point F | (3) Apparent modulus of elasticity Ed | (4) Stress difference H | (5) Residual strain Z | Characteristics and effects when used as medical guidewire |
| — | None | Large | — | — | Good pushability → able to be inserted close to end |
| — | — | — | — | Small | Good in shape recovery → able to be re-inserted (reused) |
| High | — | — | Small | — | Good torque transmission → improved steerability |

As shown in Table 1, in the shape and characteristics of the stress-strain curve in a wire tensile test, when there is no yield point, the larger the apparent modulus of elasticity Ed, the better the pushability and the more the guidewire can be In the above cold drawing, intermediate annealing is suitably carried out, but the cold-wire is finally cold drawn. The reduction rate of the drawn wire to be mechanically straightened is appropriately 10 to 60%.

Note that the method of production of the present invention is fundamentally different from the method of production of a superelastic wire of the related art (hot working→cold drawing→heat treatment for giving superelasticity), the method of production of a cold drawn, hardened wire (hot working→cold drawing), and the method of production of a cold drawn, low temperature heat-treated wire.

Namely, the method of production of the present invention mechanically straightens a cold drawn NiTi-based alloy wire under conditions of a torsional shear strain of 2 to 50%, a temperature of 100 to 275° C., and the range of abcdefg shown in FIG. 7. While applying a tension of 18 kgf/mm² or more so as to obtain a medical guidewire having the characteristics (1) to (5) described in the above first aspect of the invention.

The above mechanical straightening is an important process most affecting the characteristics of the obtained NiTi-based alloy wire.

The mechanical straightening in the present invention is performed in the predetermined range of torsional shear strain and temperature shown in FIG. 7 while applying a tension of 18 kgf/mM².

The reason why the above tension was set to 18 kgf/mm² or more and the conditions of the torsional shear strain and temperature were set as such is because an NiTi-based alloy wire having the above characteristics (1) to (5) cannot be obtained outside the range of these conditions.

For example, when the temperature of the wire under being worked exceeds 275° C., a yield point due to stress-induced martensitic transformation appears, the stress difference becomes large, and characteristics at use such as the pushability and torque transmission decline.

Also, when the temperature is less than 100° C., sufficient straightness cannot be obtained.

Also, the maximum limit of the torsional shear strain (ag in FIG. 7) was set to 50% because the wire breaks in the straightening when exceeding the level.

Note that the tension at the mechanical straightening is 18 kgf/mm² or more, but suitably is about 50 to 170 kgf/mm².

The twisting in the present invention is performed using the method comprising, as shown in FIGS. 8 and 9, heating the wire in a heating furnace, fixing one end of the wire 9 by a fixing member 10, applying tension by a weight 11 on the other end, and turning either one of the fixed side or weighted side.

Also, as shown in FIG. 10, it is possible to apply tension on the wire 9 wound on a bobbin 14 and pass it though the heating furnace 12 and, while doing so rotate the bobbin to give torsion to the wire so as to enable continuous production. The method of production shown in FIG. 8 is the most preferable in terms of productivity.

Furthermore, a spinner type straightener or a blade type straightener etc. which add a slight bending to the twisting can be also used.

In that case, if not heating by the heating furnace as explained above, heat is generated by friction between the fast spinning straighteningtop and the wire, so the wire substantially becomes the temperature of the present invention and a medical guidewire of the present invention is obtained in some cases.

Note that since the dislocation of strain introduced by the twisting differs in direction from the dislocation introduced by cold drawing, the residual strain can be eased and dislocation density can be increased, so a wire where almost no permanent deformation occurs even if large strain of 4% is given and satisfying the other required values of (1) to (5) can be obtained.

In the present invention, the mechanical straightening giving torsional strain is the most important process in obtaining the characteristics of the wire of the present invention. A just cold drawn wire does not have any yield points or inflection points, but straightness of the wire cannot be obtained. Further, when a strain of 4% is given, permanent deformation occurs and the residual strain is large. Such a guidewire permanently deforms when passed through a blood vessel having a sharp curve and can no longer be inserted further. Thus, a cold drawn wire cannot be used as a medical guidewire.

This is further improved by the mechanical straightening of the present invention. By leaving dislocation due to working strain in a direction other than the wire drawing direction (circumferential direction with respect to wire) by the straightening, it is possible to obtain the superior characteristics of the present invention, that is, a high straightness, large apparent modulus of elasticity, and small residual strain.

BRIEF DESCRIPTION OF THE DRAWINGS

FIG. 1 gives explanatory view of a variety of stress-strain curves in tensile tests of a metal wire, wherein FIG. 1B shows the case of a cold drawn NiTi-based wire, FIG. 1C the case of a cold drawn, low temperature heat-treated NiTi-based wire, FIG. 1D a superelastic wire, and FIG. 1E a highly worked stainless steel wire.

DETAILED DESCRIPTION OF PREFERRED EMBODIMENTS

EXAMPLES

BEST MODE FOR CARRYING OUT THE INVENTION

Below, embodiments of the present invention will be explained in detail by a comparison with comparative examples and conventional examples.

Below, a first embodiment of the present invention will be explained.

First Embodiment

Cast ingots of an NiTi-based alloy containing 51.0 at % of Ni and the remainder of Ti (Sample Nos. 1 to 10 shown in Table 2) were hot worked and cold drawn to produce wires having a diameter of 0.35 mm with a final cold working rate of 55% after annealing in the above cold drawing.

Figure 10:
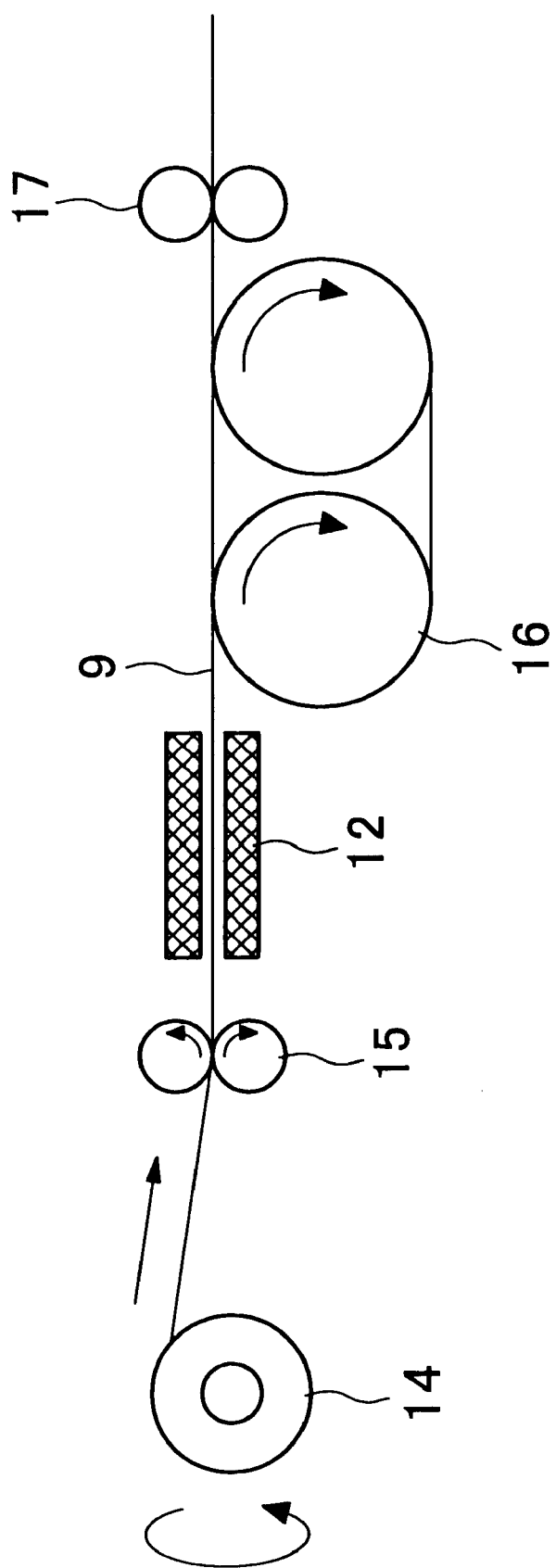
FIG. 10 is another example of continuous mechanical straightening of the present invention.

These were mechanically straightened by rotation of the bobbin shown in FIG. 10 to produce medical guidewires.

Figure 7:
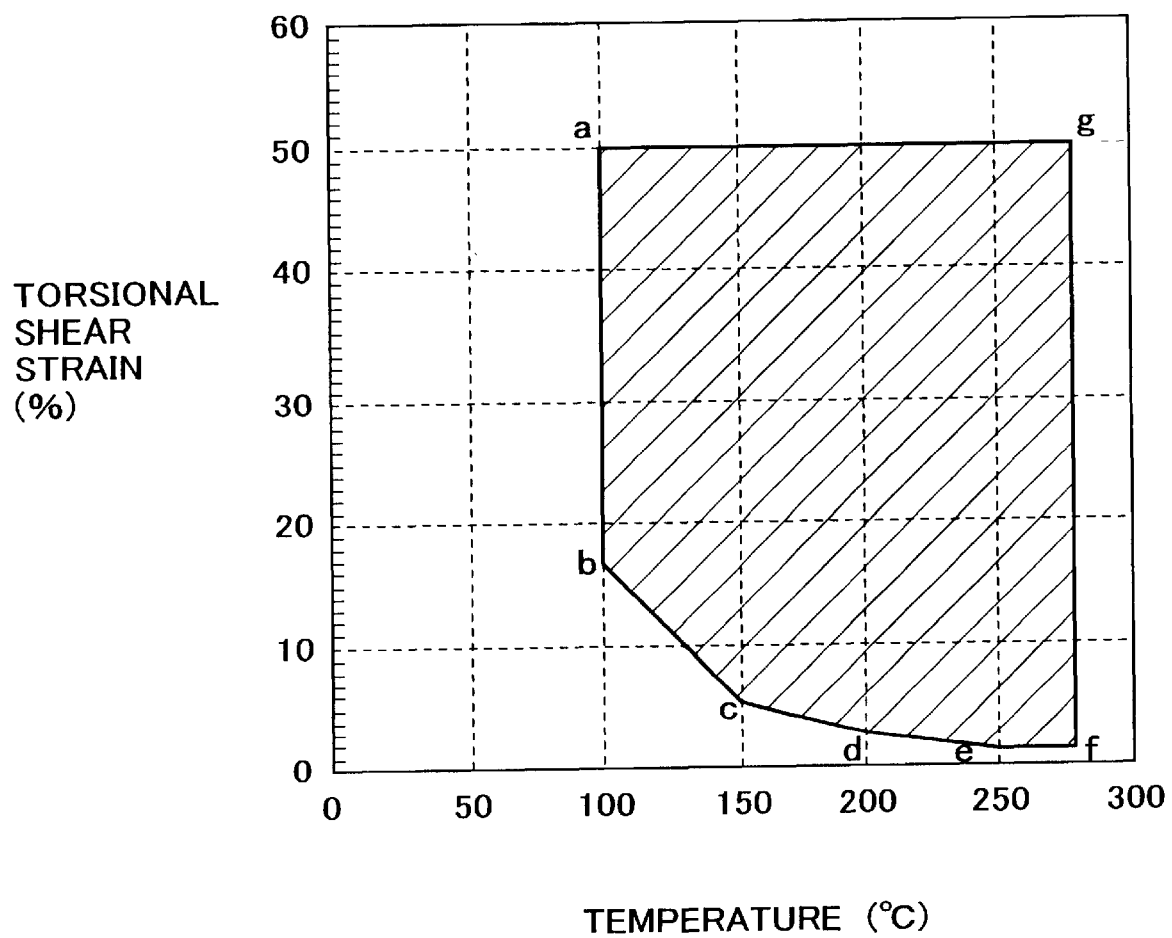
FIG. 7 is an explanatory view of the range abcdef of conditions of the torsional shear strain and temperature in mechanical straightening in the present invention.
Figure 8:
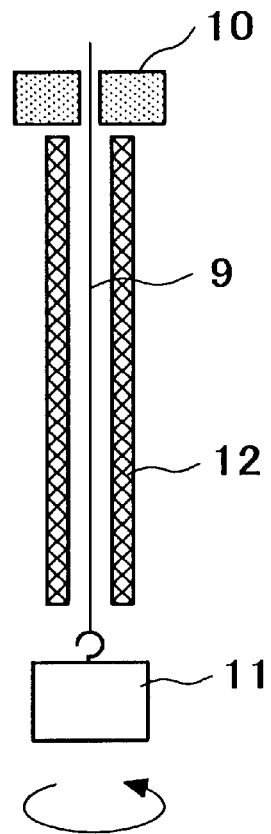
FIG. 8 is an example of mechanical straightening in the present invention.
Figure 9:
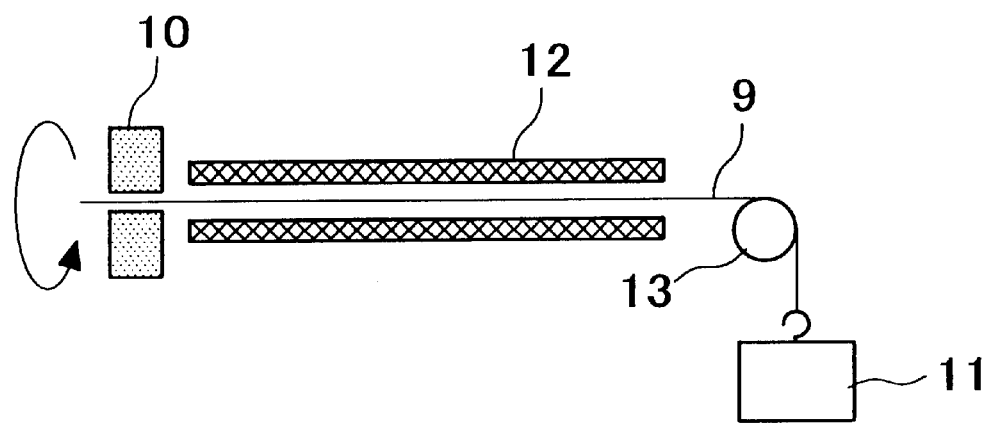
FIG. 9 is another example of mechanical straightening in the present invention.

In the above mechanical straightening, the tension was set to 75 kgf/mm$^2$ and the torsional shear strain and temperature were set so that the relationship of the two came within the range of abcdefg in FIG. 7.

Also, medical guidewires were produced by the same method as described above except for using a Cr alloy cast ingot of 48.9 at % of Ni and 0.2 at % of Ti (Sample No. 11 shown in Table 2) and an Fe alloy cast ingot of 50.0 at % of Ni, 8.0 at % of Ti, and 0.2 at % of Cu (Sample No. 12 shown in Table 2), a

Comparative Examples

Next, as comparative examples, cast ingots of NiTi alloy containing 51.0 at % of Ni and the remainder of Ti (Sample Nos. 13 to 22) were hot worked and cold drawn to produce wires having a diameter of 0.35 mm with a final cold working rate of 55% after annealing in the above cold drawing.

These were mechanically straightened by rotation of the bobbin shown in FIG. 10 to produce medical guidewires.

In the above mechanical straightening, the tension was set to 75 kgf/mm$^2$ and the torsional shear strain and temperature were set to give a relationship of the two out of the range of abcdefg (below bcdef) In FIG. 7 to produce comparative medical guidewires.

The production conditions of the examples of the invention and comparative examples are shown in Table 2.

Conventional Examples

NiTi alloy (Sample Nos. 23 to 25) cast ingots containing 51.0 at % of Ni and the remainder of Ti were processed in the same way as Sample No. 1 up to the cold working.

Sample No. 23 is a test material only cold drawn (cold drawn wire).

Sample No. 24 is a cold drawn, low temperature heat-treated wire obtained by heat treating a cold drawn material at a low temperature (350° C. for 10 seconds).

Sample No. 25 is a superelastic wire obtained by heat treating a cold drawn material (420° C. for 60 seconds).

Sample No. 26 is a stainless steel wire having a drawing rate of 57%.

Figure 3:
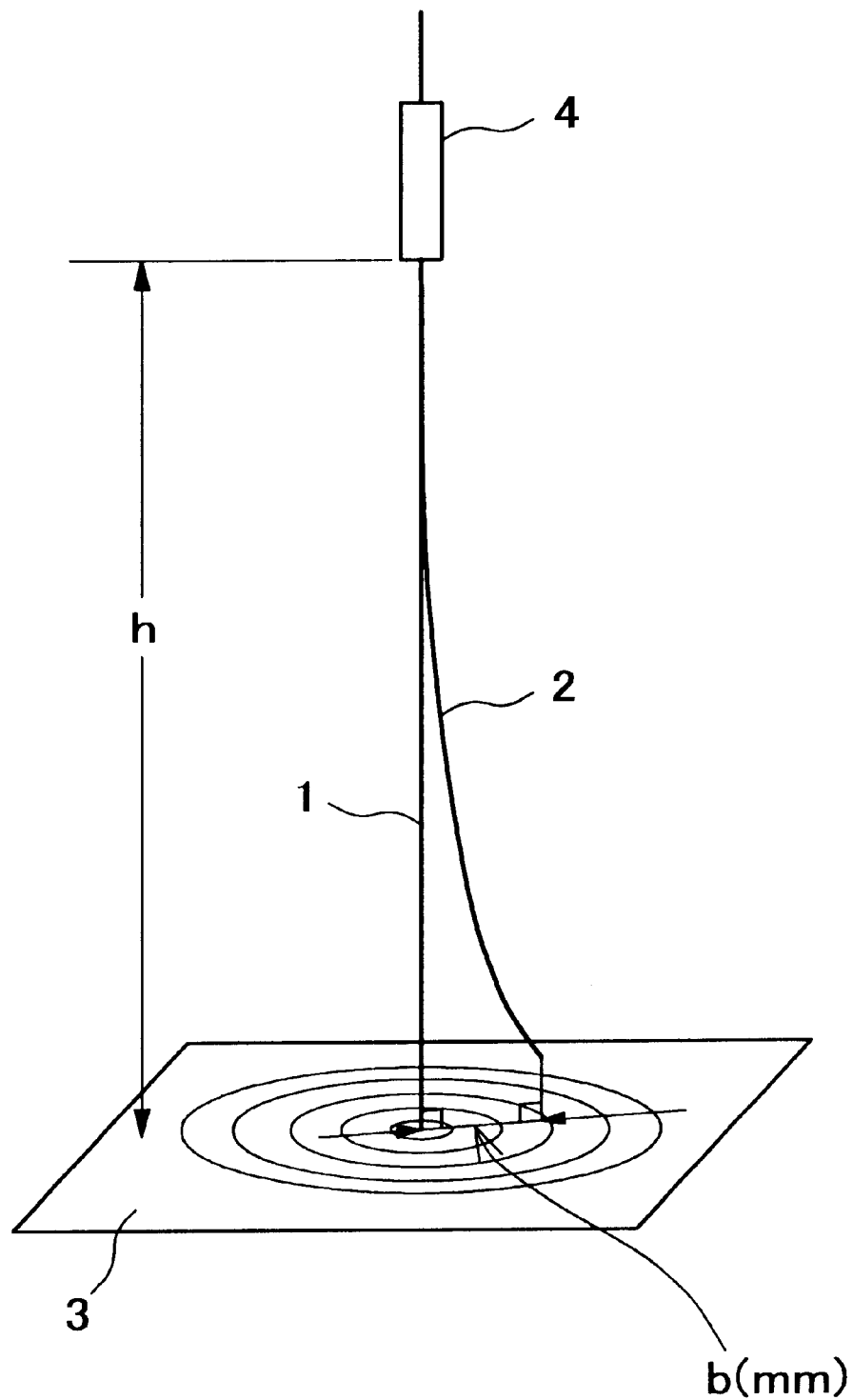
FIG. 3 is an explanatory view of the method of finding the straightness by the method of suspending a medical guidewire.
Figure 4:
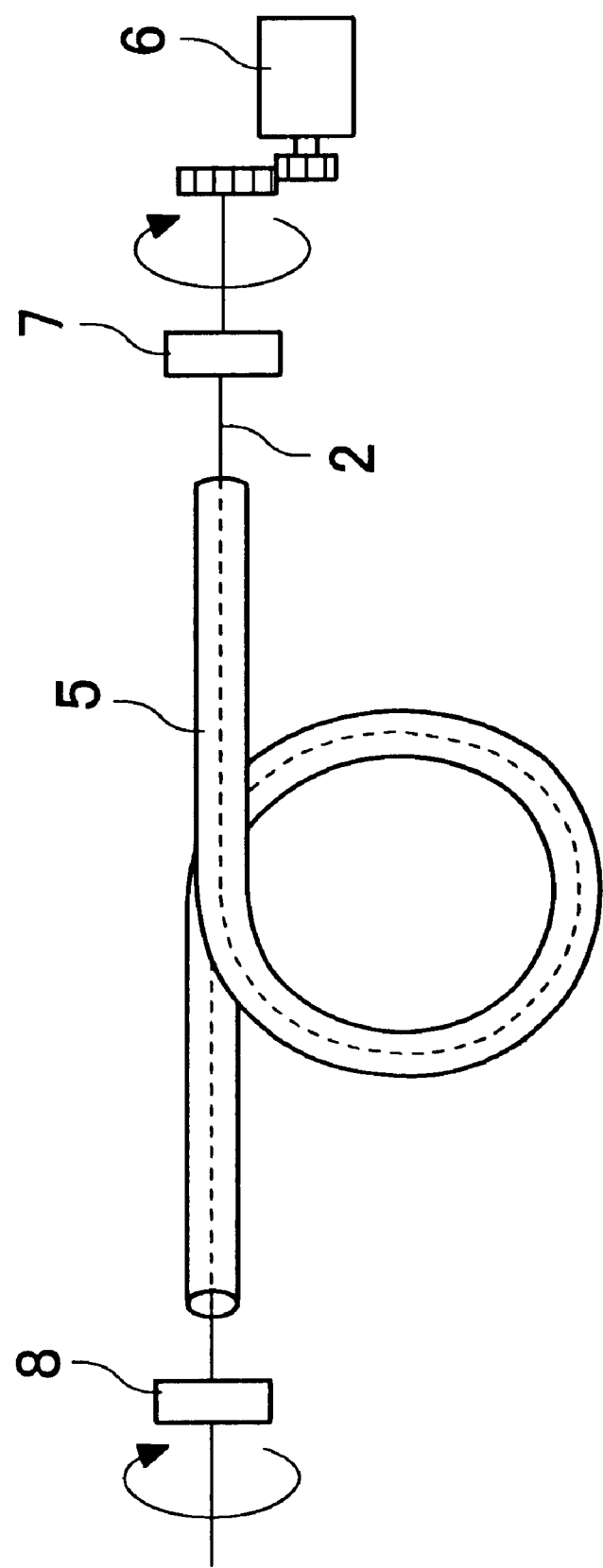
FIG. 4 is an explanatory view of the method of measuring the torque transmission.
Figure 5:
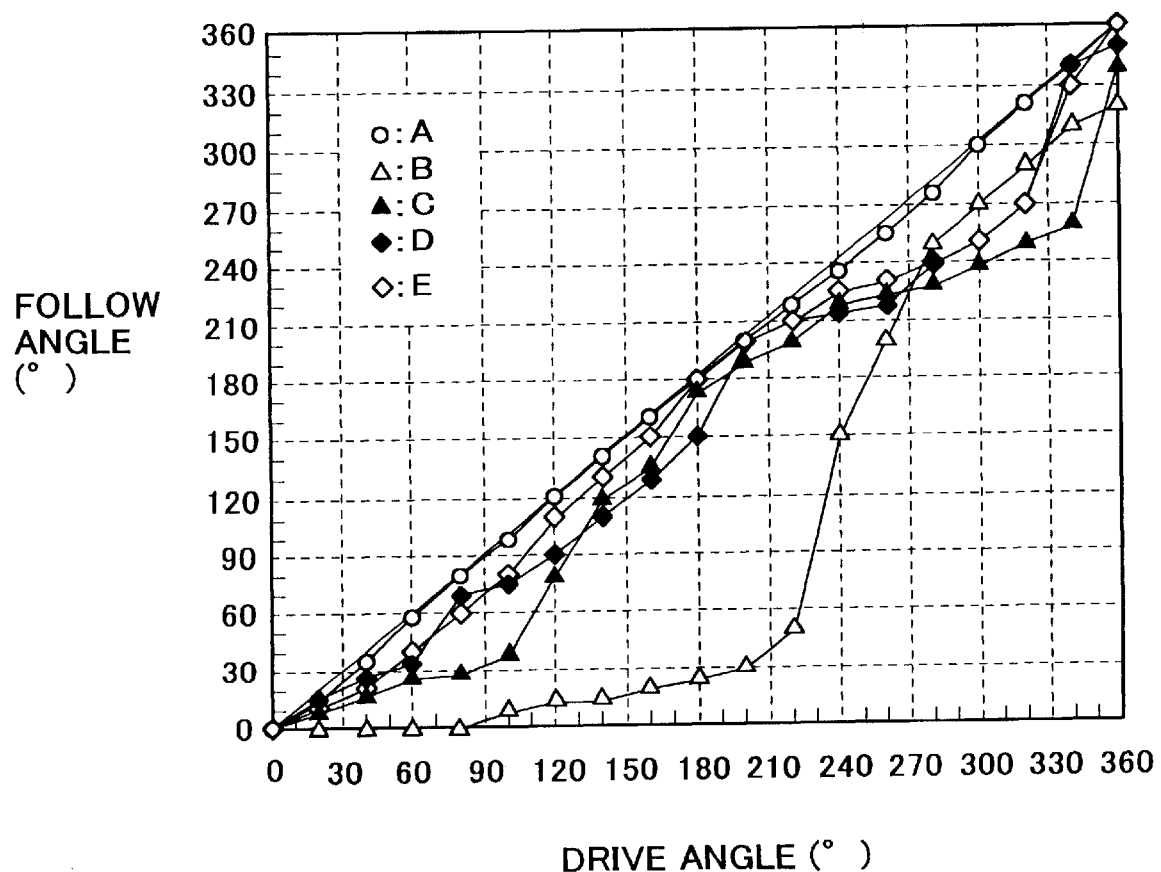
FIG. 5 is a view of the relationship of a drive angle and a follow angle showing the torque transmission.
Figure 6A:
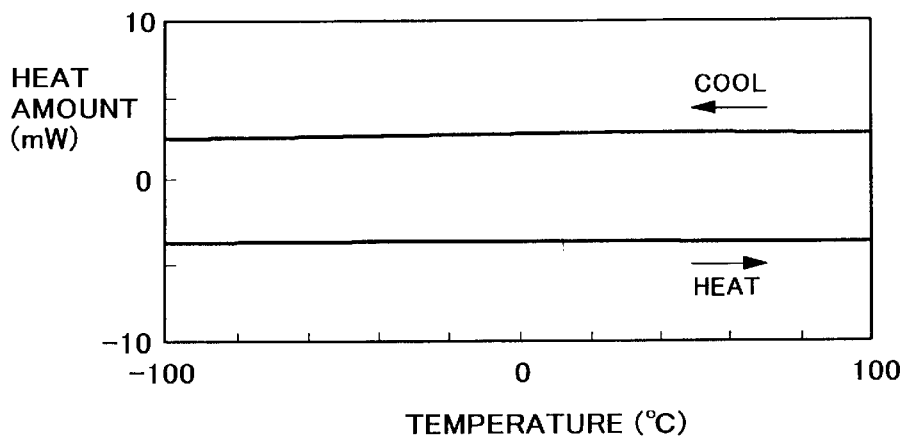
FIG. 6 is a view of the change in heat in differential scan calorimetry (DSC) for investigating phase transformation and structural changes of an alloy wire, wherein (A) shows the case of an NiTi-based wire. Also, (C) shows the case of a cold drawn, low temperature heat-treated type NiTi wire and (D) a superelastic NiTi-based wire.
Figure 6C:
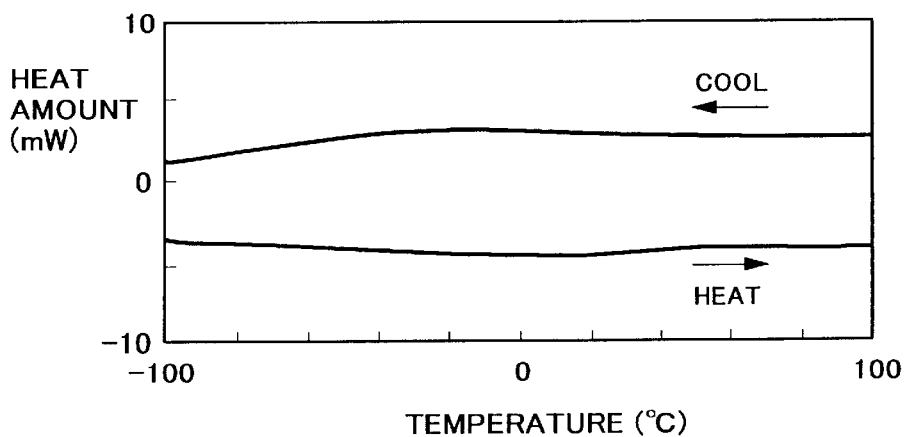
Figure 6D:
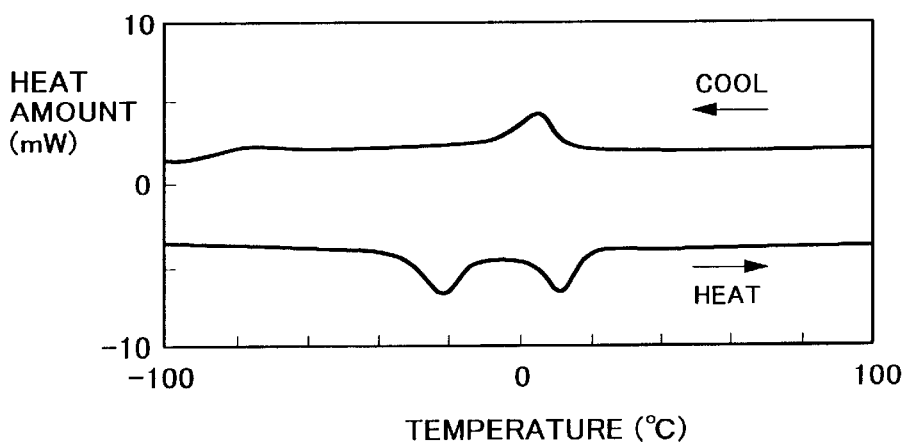

The thus produced test wires were measured for the (1) straightness b of the wires. The straightness was measured by the suspension method shown in FIG. 3 as explained above.

Also, a tensile test was conducted for each of the test wires to find the stress-strain curve. The (2) shape of the stress-strain curve up to the strain of 4%, (4) the stress difference H (stress hysteresis) at a strain of 2% after deformation up to the strain of 4% and then removal of the stress, (5) the residual strain Z after deformation up to 4% were then found.

The test results are shown all together in Table 2.

TABLE 2

| | | | | | Characteristics of guidewire | | | | | |
| --- | --- | --- | --- | --- | --- | --- | --- | --- | --- | --- |
| | | | | | Characteristics of stress-strain curve | | | | | |
| | Mechanical straightening | | | | (3) Apparent | | | | | |
| | | | Torsional | (1) | modulus of | (4) Stress | (5) | | Characteristics in use | |
| Sample no. | Temp. (° C.) | Tension (kgf/mm$^2$) | shear strain (%) | Straightness b (mm) | elasticity Ed (kgf/mm$^2$) | difference H (kgf/mm$^2$) | Residual strain (%) | Pushability | Torque transmission | Reusability |
| Inv. Ex. | | | | | | | | | | |
| 1 | 100 | 75 | 17.0 | 19.0 | 3470 | 12.8 | 0.10 | Good | Good | Good |
| 2 | 100 | 75 | 23.0 | 15.0 | 3530 | 12.6 | 0.10 | Good | Good | Good |
| 3 | 100 | 75 | 25.0 | 13.0 | 3490 | 12.7 | 0.09 | Good | Good | Good |
| 4 | 150 | 75 | 10.0 | 7.5 | 3390 | 12.8 | 0.06 | Good | V. Good | Good |
| 5 | 150 | 75 | 15.0 | 3.8 | 3330 | 12.7 | 0.07 | Good | V. Good | Good |
| 6 | 200 | 75 | 2.5 | 20.0 | 3380 | 12.4 | 0.05 | Good | Good | Good |
| 7 | 200 | 75 | 5.0 | 12.0 | 3290 | 12.6 | 0.04 | Good | Good | Good |
| 8 | 200 | 75 | 10.0 | 3.0 | 3340 | 12.9 | 0.04 | Good | V. Good | Good |
| 9 | 260 | 75 | 2.5 | 8.0 | 3130 | 11.1 | 0.01 | Good | V. Good | Good |
| 10 | 260 | 75 | 5.0 | 2.0 | 3100 | 11.0 | 0.02 | Good | V. Good | Good |
| 11 | 260 | 75 | 10.0 | 10.0 | 3300 | 11.0 | 0.07 | Good | V. Good | Good |
| 12 | 250 | 75 | 5.0 | 3.0 | 3500 | 10.5 | 0.04 | Good | V. Good | Good |
| Comp. Ex. | | | | | | | | | | |
| 13 | 50 | 75 | 10.0 | 150.0 | 3550 | 18.7 | 0.19 | Good | Poor | Fair |
| 14 | 50 | 75 | 20.0 | 65.0 | 3690 | 16.5 | 0.16 | Good | Poor | Fair |
| 15 | 50 | 75 | 30.0 | 51.0 | 3660 | 17.2 | 0.17 | Good | Poor | Fair |
| 16 | 100 | 75 | 0.0 | 135.0 | 3700 | 12.3 | 0.10 | Good | Poor | Good |
| 17 | 100 | 75 | 5.0 | 75.0 | 3500 | 12.1 | 0.09 | Good | Poor | Good |
| 18 | 100 | 75 | 10.0 | 37.5 | 3630 | 12.6 | 0.10 | Good | Fair | Good |
| 19 | 150 | 75 | 0.0 | 75.0 | 3340 | 11.9 | 0.08 | Good | Poor | Good |
| 20 | 150 | 75 | 5.0 | 22.5 | 3380 | 12.4 | 0.07 | Good | Fair | Good |
| 21 | 200 | 75 | 0.0 | 37.5 | 3220 | 11.8 | 0.04 | Good | Fair | Good |

TABLE 2-continued

| | Mechanical straightening | | | | Characteristics of guidewire | | | Characteristics in use | | |
|---|---|---|---|---|---|---|---|---|---|---|
| | | | Torsional | (1) | Characteristics of stress-strain curve | | | | | |
| | | | | | (3) Apparent | (4) Stress | (5) | | | |
| Sample no. | Temp. (° C.) | Tension (kgf/mm²) | shear strain (%) | Straightness b (mm) | modulus of elasticity Ed (kgf/mm²) | difference H (kgf/mm²) | Residual strain (%) | Pushability | Torque transmission | Reusability |
| 22 Conv. Ex. | 260 | 75 | 0.0 | 25.0 | 3090 | 10.8 | 0.02 | Good | Pair | Good |
| 23 | | Cold drawn | | 105.0 | 4472 | 37.4 | 0.40 | Good | Poor | Poor |
| 24 | Cold drawn lov temp. heat-treated | | | 70.0 | 2875 | 45.5 | 0.02 | Fair | Poor | Good |
| 25 | | Superelastic | | 30.0 | 1568 | 29.7 | 0.07 | Poor | Fair | Good |
| 26 | High worked stainless steel wire | | | 30.0 | Broke at 1.8% strain | | | Poor | Fair | Poor |

Note: Nos. 1 to 10 and Nos. 13 to 25 are Ni—Ti alloys. No. 11 is Ni—Ti—Cr alloy, and No. 12 is Ni—Ti—Cu—Fe alloy.

Figure 1A:
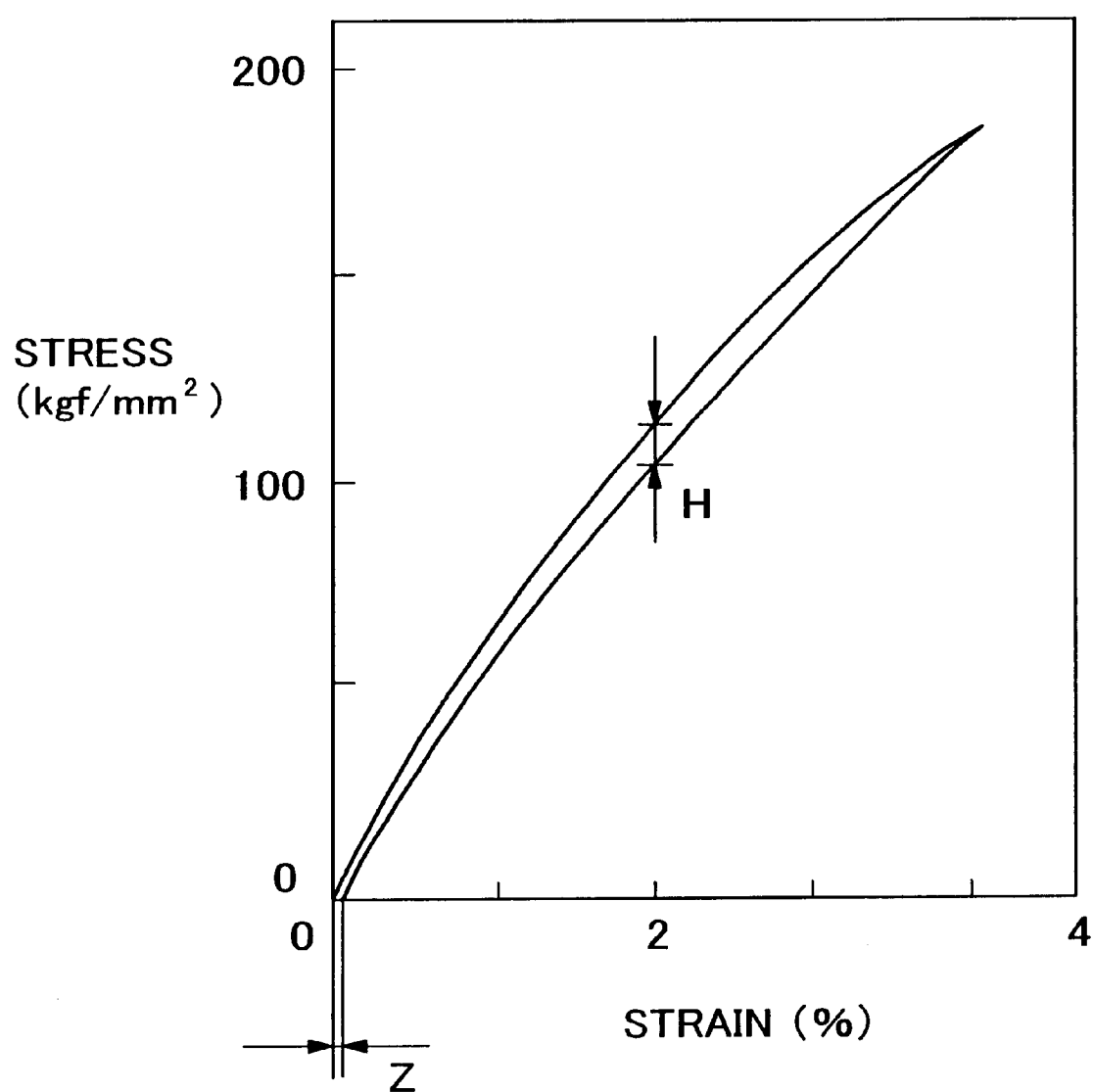
FIG. 1A shows the case of an NiTi-based wire of the present invention.

The (2) shapes of the stress-strain curves up to a strain of 4% of the examples of the present invention (Sample Nos. 1 to 12) and comparative examples (Sample Nos. 13 to 22) were by and large the same as in FIG. 1A.

Also, the (2) shapes of the stress-strain curves up to a strain of 4% of Sample Nos. 23 to 26 of the conventional examples were as shown in FIGS. 1B, 1C, 1D, and 1E, respectively.

As clear from the test results of Table 2, it was confirmed that the guidewires of the present invention were superior in all of the characteristics of (1) straightness, (3) apparent modulus of elasticity, (4) stress difference, and (5) residual strain as characteristics of the stress-strain curve and exhibited pushability, torque transmission, and reusability as characteristics of use as a medical guidewire.

As opposed to this, the guidewires of the comparative examples (Sample Nos. 13 to 22) were poor in some of the characteristics of use since one or more the characteristics as a guidewire were out of the range of the present invention.

Also, as clear from the Table 2, the guidewires of the conventional examples (Sample Nos. 23 to 26) were inferior in one or more the characteristics as a guidewire, so were poor in one or more of the characteristics of use as a medical guidewire.

Second Embodiment

Cast ingots of an NiTi alloy containing 51.0 at % of Ni and the remainder of Ti (Sample Nos. 31 to 39 shown in Table 3) were hot worked and cold drawn to produce wires having a diameter of 0.35 mm with a final cold working rate of 55% after annealing in the above cold drawing.

These were mechanically straightened by rotation of the bobbin shown in FIG. 10 to produce medical guidewires.

In the above mechanical straightening, the tension was changed between 18 to 170 kgf/mm², the torsional shear strain was made 20% or 30%, and the temperature was made 100° C. or 200° C.

Comparative Examples

The same procedure was followed as in the second embodiment to produce medical guidewires (Sample Nos. 40 to 42 in Table 3) except for making the tension in the mechanical straightening less than 18 kgf/mm², which is out of the range of the present invention.

The test wires were tested and evaluated in the same way as the first embodiment. The results are shown in Table 3.

TABLE 3

| | Mechanical straightening | | | | Characteristics of guidewire | | | Characteristics in use | | |
|---|---|---|---|---|---|---|---|---|---|---|
| | | | Torsional | (1) | Characteristics of stress-strain curve | | | | | |
| | | | | | (3) Apparent | (4) Stress | (5) | | | |
| Sample no. | Temp. (° C.) | Tension (kgf/mm²) | shear strain (%) | Straightness b (mm) | modulus of elasticity Ed (kgf/mm²) | difference H (kgf/mm²) | Residual strain (%) | Pushability | Torque transmission | Reusability |
| Inv. Ex. | | | | | | | | | | |
| 31 | 100 | 50 | 30.0 | 15.0 | 3590 | 12.7 | 0.08 | Good | Good | Good |
| 32 | 100 | 100 | 30.0 | 15.0 | 3570 | 12.8 | 0.10 | Good | Good | Good |
| 33 | 100 | 147 | 30.0 | 14.0 | 3600 | 12.6 | 0.09 | Good | Good | Good |
| 34 | 100 | 170 | 30.0 | 13.0 | 3630 | 12.6 | 0.10 | Good | Good | Good |
| 35 | 200 | 18 | 20.0 | 15.0 | 3290 | 12.3 | 0.05 | Good | Good | Good |
| 36 | 200 | 50 | 20.0 | 7.0 | 3280 | 12.4 | 0.06 | Good | V. Good | Good |
| 37 | 200 | 100 | 20.0 | 5.0 | 3320 | 12.5 | 0.05 | Good | V. Good | Good |
| 38 | 200 | 147 | 20.0 | 3.0 | 3330 | 12.2 | 0.05 | Good | V. Good | Good |
| 39 | 200 | 170 | 20.0 | 3.0 | 3370 | 12.0 | 0.06 | Good | V. Good | Good |

TABLE 3-continued

| | | Mechanical straightening | | | Characteristics of guidewire | | | | | |
|---|---|---|---|---|---|---|---|---|---|---|
| | | | | | Characteristics of stress-strain curve | | | | | |
| | | | | | (3) Apparent | | | | Characteristics in use | |
| Sample no. | Temp. (° C.) | Tension (kgf/mm²) | Torsional shear strain (%) | (1) Straightness b (mm) | modulus of elasticity Ed (kgf/mm²) | (4) Stress difference H (kgf/mm²) | (5) Residual strain (%) | Pushability | Torque transmission | Reusability |
| Comp. Ex. | | | | | | | | | | |
| 40 | 100 | 10 | 30.0 | 200.0 | 3440 | 12.7 | 0.08 | Good | Poor | Good |
| 41 | 100 | 15 | 30.0 | 25.0 | 3510 | 13.0 | 0.09 | Good | Fair | Good |
| 42 | 200 | 10 | 20.0 | 180.0 | 3260 | 12.3 | 0.04 | Good | Poor | Good |

Figure 2:
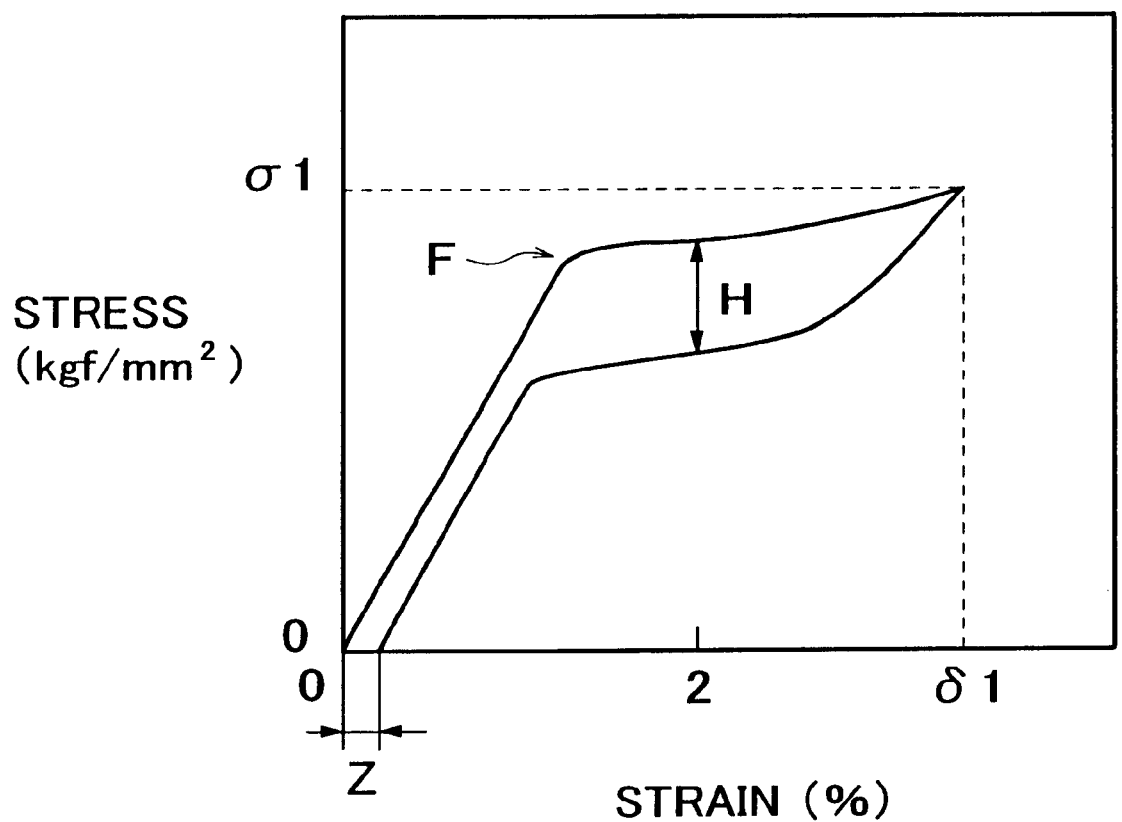
FIG. 2 is a view of a general stress-strain curve in a tensile test of an NiTi-based alloy showing a yield point F, an apparent modulus of elasticity $Ed=\sigma 1/\delta 1$, a stress difference H, and a residual strain Z.

Note that the (2) shapes of the stress-strain curves up to a strain of 4% of the examples of the present invention and comparative examples were substantially the same as in FIG. 2A.

As clear from the test results of Table 3, it was confirmed that the guidewires of the present invention (Sample Nos. 31 to 39) are superior in all of the characteristics of (1) straightness, (3) apparent modulus of elasticity, (4) stress difference, and (5) residual strain as characteristics of the stress-strain curve and exhibit pushability, torque transmission, and reusability as characteristics in use as a medical guidewire.

As opposed to this, the guidewires of the comparative examples (Sample Nos. 40 to 42) were found to be inferior in one or more of the characteristics in use since one or more of the characteristics as a guidewire were out of the range of the present invention.

As explained above, a method of producing an NiTi-based guidewire of the present invention and an NiTi-based guidewire obtained by the method of production of the same give excellent pushability, torque transmission, and reusability as catheter or other guidewires and therefore suitability as a medical guidewire.

INDUSTRIAL APPLICABILITY

A medical guidewire of the present invention is used for a catheter guidewire, endoscope guidewire, etc.

LIST OF REFERENCE NUMERALS

1 COMPLETELY STRAIGHT WIRE
2 TEST WIRE OF TOTAL LENGTH OF 1.5 M
3 FLOOR SURFACE
H DISTANCE (1.5 M) IN CASE OF COMPLETELY STRAIGHT WIRE
B DISTANCE INDICATING STRAIGHTNESS OF WIRE
4 WIRE HOLDER (MADE OF SUS)
5 POLYETHYLENE TUBE
6 MOTOR
7 ROTARY ENCODER ON DRIVE SIDE
8 ROTARY ENCODER ON FOLLOWING SIDE
9 PRODUCED WIRE
10 HOLDER
11 WEIGHT
12 HEATING FURNACE
13 PULLEY
14 BOBBIN
15 PINCH ROLLER
16 CAPSTAN
17 PINCH ROLLER

What is claimed is:

1. An NiTi-based medical guidewire comprising an NiTi-based alloy wire made of a wire produced by mechanical straightening a cold drawn NiTi-based alloy wire and (1) having a straightness of 20 mm/1.5 m as determined by the suspension method and having a shape and characteristics of the stress-strain curve in a wire tensile test which satisfy the following requirements (2) to (5) and thereby displaying excellent pushability, torque transmission, and reusability as a medical guidewire:

(2) a monotonous increase in loading up to a strain of 4% without any yield points or inflection points and no stress-induced martensitic transformation shown at all;

(3) high elasticity characteristics over a wide range of strain and an apparent modulus of elasticity of 3000 kgf/mm² or more at a strain of 4%;

(4) a residual strain after loading up to a strain of 4%, then unloading, of not more than 0.15%; and (5) a stress difference, between loading and unloading, at a strain of 2% after loading up to 4% strain, then unloading, of not more than 15 kgf/mm².

2. An NiTi-based medical guidewire as set forth in claim 1, wherein the apparent modulus of elasticity at a strain of 4% in the requirement (3) is 3500 kgf/mm² or more and the residual strain after loading a strain of 4% and unloading is not more than 0.10%.

3. An NiTi-based medical guidewire as set forth in claim 1, wherein the NiTi-based alloy wire comprises one of an NiTi alloy containing 50.2 to 51.5 at % of Ni and a remainder of Ti, an NiTi-based alloy containing 49.8 to 51.5 at % of Ni and 0.1 to 2.0 at % of at least one element selected from Cr, Fe, V, Al, Cu, Co, and Mo, and a remainder of Ti, and an NiTi-based alloy containing 49.0 to 51.0 at % of Ni, 5 to 12 at % of Cu, 0.1 to 2.0 at % of at least one of Cr, Fe, V, Al, Cu, Co, and Mo, and the remainder of Ti.

4. An NiTi-based medical guidewire as set forth in claim 1, wherein the medical guidewire is a catheter guidewire or is used for at least a part of a catheter guidewire.

5. An NiTi-based medical guidewire as set forth in claim 1, wherein the medical guidewire is an endoscope guidewire or is used for at least a part of an endoscope guidewire.

6. A method of producing an NiTi-based medical guidewire comprising an NiTi-based alloy wire made of a wire produced by mechanical straightening a cold drawn NiTi-based alloy wire and (1) having a straightness of 20 mm/1.5 m as determined by the suspension method and having a shape and characteristics of the stress-strain curve in a wire tensile test which satisfy the following requirements (2) to (5) and thereby displaying excellent pushability, torque transmission, and reusability as a medical guidewire:

(2) a monotonous increase in loading up to a strain of 4% without any yield points or inflection points and no stress-induced martensitic transformation shown at all;

(3) high elasticity characteristics over a wide range of strain and as apparent modulus of elasticity of 3000 kgf/mm² or more at a strain of 4%;

(4) a residual strain after loading up to a strain of 4%, then unloading, of not more than 0.15%; and (5) a stress difference, between loading and unloading, at a strain of 2% after loading up to 4% strain, then unloading, of not more than 15 kgf/mm², the method including a step of applying a tension of 18 kgf/mm² or more to a cold drawn NiTi-based alloy wire and mechanically straightened it under conditions defined by the relationship of a torsional shear strain (TSS) and a temperature (T) and within a domain defined a polygon of points a-b-c-d-e-f-g-a, where a is a point of TSS=50% at T=100° C.,
b is a point of TSS=17% at T=100° C.,
c is a point of TSS=5% at T=150° C.,
d is a point of TSS=2.5% at T=200° C.,
e is a point of TSS=2.0% at T=250° C.,
f is a point of TSS=2.0% at T=275° C., and
g is a point of TSS=50% at T=275° C.

7. A method of producing an NiTi-based medical guidewire as set forth in claim 6, wherein a cold working rate of the NiTi-based alloy wire supplied for the mechanical straightening is 10 to 60%.

8. A method of producing an NiTi-based medical guidewire as set forth in claim 6, wherein said tension is 50 to 170 kgf/mm².

9. A method of producing an NiTi-based medical guidewire as set forth in claim 6, wherein said mechanical straightening of the NiTi-based alloy wire is performed by applying tension on a wire wound on a bobbin and rotating the bobbin to give torsional strain to the wire while passing it through a heating furnace for continuous mechanical straightening.

* * * * *